United States Patent
Cooke et al.

(10) Patent No.: US 7,633,057 B2
(45) Date of Patent: Dec. 15, 2009

(54) PMT GAIN AND ENERGY CALIBRATIONS USING LUTETIUM BACKGROUND RADIATION

(75) Inventors: Steven Cooke, Garfield Heights, OH (US); Thomas Laurence, North Royalton, OH (US)

(73) Assignee: Koninklijke Philips Electronics N.V., Eindhoven (NL)

(*) Notice: Subject to any disclaimer, the term of this patent is extended or adjusted under 35 U.S.C. 154(b) by 0 days.

(21) Appl. No.: 12/088,087

(22) PCT Filed: Sep. 15, 2006

(86) PCT No.: PCT/IB2006/053314

§ 371 (c)(1),
(2), (4) Date: Mar. 26, 2008

(87) PCT Pub. No.: WO2007/046012

PCT Pub. Date: Apr. 26, 2007

(65) Prior Publication Data

US 2008/0251709 A1    Oct. 16, 2008

Related U.S. Application Data

(60) Provisional application No. 60/728,433, filed on Oct. 17, 2005.

(51) Int. Cl.
*G01T 1/20* (2006.01)
(52) U.S. Cl. .................. 250/252.1; 250/370.11
(58) Field of Classification Search .......... 250/252.1, 250/363.03, 363.09
See application file for complete search history.

(56) References Cited

U.S. PATENT DOCUMENTS

| | | | |
|---|---|---|---|
| 4,958,080 A | 9/1990 | Melcher | |
| 5,025,151 A | 6/1991 | Melcher | |
| 5,164,041 A | 11/1992 | Berkstresser et al. | |
| 5,218,202 A * | 6/1993 | Evers | 250/252.1 |
| 5,690,731 A | 11/1997 | Kurata et al. | |
| 5,986,266 A | 11/1999 | Andreaco et al. | |
| 6,278,832 B1 | 8/2001 | Zagumennyi et al. | |
| 6,288,399 B1 | 9/2001 | Andreaco et al. | |
| 6,323,489 B1 | 11/2001 | McClellan | |
| 6,413,311 B2 | 7/2002 | Melcher et al. | |
| 6,624,420 B1 | 9/2003 | Chai et al. | |
| 6,749,761 B1 | 6/2004 | Andreaco et al. | |
| 6,818,896 B2 | 11/2004 | Pauwels et al. | |

(Continued)

OTHER PUBLICATIONS

Wang, et al., "Calibration of a PEM Detector with Depth of Interaction Measurement," IEEE Trans. on Nuclear Science, 51(3), Jun. 2004, pp. 775-781.

(Continued)

*Primary Examiner*—David P Porta
*Assistant Examiner*—Marcus H Taningco (57) ABSTRACT

A scintillator (18) includes radioactive elements which emit radiation of a characteristic energy, such as lutetium$^{176}$, which emits 202 keV and 307 keV γ-rays. The scintillators have light output levels that vary and photomultiplier tubes that respond to the light scintillations tend to drift. When a scanner (10) is not generating diagnostic images, the photomultiplier tubes detect scintillations from the lutetium 176 radiation. A self-calibration processor (40) adjusts the gain for each photomultiplier tube such that its output peak corresponds to 202 keV or 307 keV and adjusts a scaling factor for PMT outputs corresponding to each scintillator such that the output peaks have a common amplitude.

18 Claims, 7 Drawing Sheets

U.S. PATENT DOCUMENTS

| | | |
|---|---|---|
| 6,921,901 B1 | 7/2005 | Chai et al. |
| 2003/0057375 A1 | 3/2003 | Williams et al. |
| 2004/0036026 A1 | 2/2004 | Engdahl et al. |
| 2005/0030601 A1 | 2/2005 | Smith et al. |
| 2006/0102845 A1 | 5/2006 | Williams et al. |
| 2006/0138315 A1 | 6/2006 | Williams et al. |

OTHER PUBLICATIONS

Yamamoto, et al., "Investigation of Single, Random, and True Counts from Natural Radioactivity in LSO-based Clinical PET," Annals of Nuclear Med., 2005, 19(2), pp. 109-114.

* cited by examiner

PMT GAIN AND ENERGY CALIBRATIONS USING LUTETIUM BACKGROUND RADIATION

CROSS REFERENCE TO RELATED APPLICATIONS

This application claims the benefit of U.S. provisional application Ser. No. 60/728,433 flied Oct. 17, 2005, which is incorporated herein by reference.

The present invention relates to the field of medical imaging. It finds particular application to the calibration of photomultiplier tubes (PMTs) in conjunction with positron emission tomography (PET) scanners, and will be described with particular reference thereto. The invention is also applicable to other imaging modalities that utilize scintillation crystals, such as SPECT, and other imaging modalities.

Generally, in medical imaging, consistency of the scanner is of paramount importance. All other things being equal, technicians would like to see that two images of the same subject using the same settings look the same. One of the most significant challenges in maintaining scanner stability in nuclear imaging is keeping the PMTs calibrated. PMT output is known to drift over time, as a result of usage and temperature. PMT drift is correctable by adjusting the electronic gain of the PMT. Generally, the outputs of a calibrated PMT and an uncalibrated PMT are the same, only shifted by energy channel. An electronic gain adjustment can bring the output of a drifted PMT back into channel alignment, however, the PMTs typically do not drift uniformly, so each PMT must be calibrated separately.

Typically, the required gain for each PMT is determined by placing a radioactive material in the scanner and running a calibration process. The radioactive calibration source produces radiation of a characteristic energy. The gain for each PMT is determined that will put the output signal from the characteristic energy radiation into the corresponding output energy channel. That gain is stored in memory and used during subsequent imaging procedures. This process is run until all of the PMTs of a system have been calibrated.

In order to perform this routine maintenance, a technician is called to perform a PMT calibration on a scanner, either at set maintenance dates, or when actual drift is impeding the production of useful medical images. This creates some unavoidable down-time for the scanner, and expense for the technician.

The present application contemplates a new and improved nuclear imaging apparatus and accompanying method that overcome the above-referenced problems and others.

In accordance with one aspect of the present invention, a diagnostic imaging apparatus is provided. A scintillating element emits light in response to incumbent radiation. The scintillating element is also inherently radioactive. An array of PMTs generates responses to incident radiation, which varies with time and among the PMTs. A PMT self-calibration processor re-calibrates the response of the PMTs using the inherent radioactivity of the scintillating element In accordance with another aspect of the present invention, a method of calibrating a diagnostic imaging scanner is provided. Background radiation is generated with an array of scintillating elements that exhibit inherent radioactivity of at least one characteristic energy. Photonic emissions are generated with the scintillating elements in response to the background radiation emitted by the scintillating elements. A response is generated to the photonic emissions with the photomultiplier tubes which response varies among the photomultiplier tubes. The photomultiplier tubes are calibrated using the response to the inherent background radiation of the scintillating elements.

In accordance with another aspect of the present invention, a diagnostic imaging apparatus is provided. At least one detector assembly, including an array of scintillators and an array of photodetectors, includes a radioactive element which emits radiation with at least one characteristic energy peak. The scintillators exhibit varying amounts of light output from the radioactivity of the characteristic energy peak. An amplitude calibration memory stores scaling factors corresponding to each scintillator for scaling photodetector outputs. A self calibration processor receives the photodetector outputs responsive to the radioactive element emitted radiation and adjusts the scaling factors to bring characteristic peak amplitudes of the photodetector outputs to a common amplitude.

In accordance with another aspect of the present invention, a diagnostic imaging apparatus is provided. The apparatus includes at least one detector assembly including photodetectors whose response characteristics drift over time. Scintillators in the detector assembly produce inherent background radiation. A self calibration processor receives the photodetector outputs responsive to the inherent background radiation and calibrates the photodetectors during down time of the imaging apparatus as a function of time.

In accordance with another aspect of the present invention, a method of calibrating a diagnostic imaging scanner is provided. Background radiation is generated with an array of scintillating elements that exhibit inherent radioactivity of at least one characteristic energy. Photonic emissions are generated with the scintillating elements in response to the background radiation emitted by the scintillating elements. A response to the photonic emissions is generated with the photomultiplier tubes which response varies among the photomultiplier tubes. The photomultiplier tubes are calibrated using at least two characteristic peaks in the response to the inherent background radiation of the scintillating elements.

One advantage of the present invention resides in reduced down time in which the scanner cannot scan patients.

Another advantage resides in elimination of service calls for PMT calibration.

Another advantage resides in continuous updating of PMT calibration.

Another advantage resides in diagnostic images generated with precise calibration.

Another advantage resides in the elimination of a need for a separate radioactive calibration source.

Still further advantages and benefits of the present invention will become apparent to those of ordinary skill in the art upon reading and understanding the following detailed description of the preferred embodiments.

The invention may take form in various components and arrangements of components, and in various steps and arrangements of steps. The drawings are only for purposes of illustrating the preferred embodiments and are not to be construed as limiting the invention.

Figure 1:
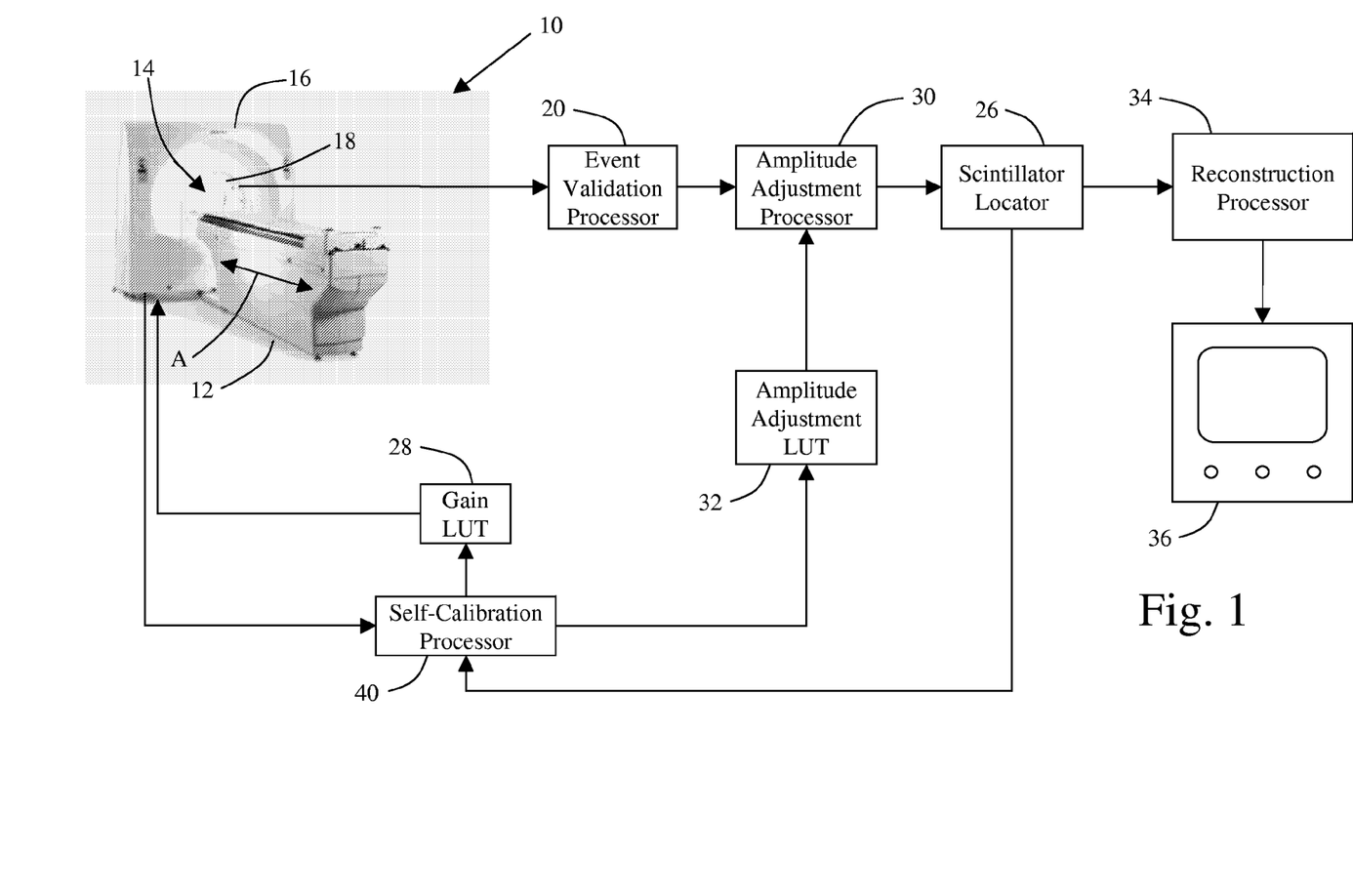
FIG. 1 is a diagrammatic illustration of a nuclear medicine scanner in accordance with the present application.

With reference to FIG. 1, a preferred embodiment of a nuclear medicine scanner 10 is shown. Prior to a scan, a subject is placed on a subject support surface 12. The subject support surface moves along its longitudinal axis A, into and out of a bore 14 of a gantry 16 of the scanner 10. The bore of a PET scanner is lined with a cylinder of radiation detectors 18. Optionally, the detectors include a plurality of detector heads, as is more typical of SPECT scanners. In either case, the detectors 18 are disposed around and along the subject receiving bore 14 to receive incident γ-rays. Typically, incident γ-rays strike the detectors 18 which preferably include an array of scintillation crystals and PMTs, although any other detectors that include scintillation crystals are contemplated. The scintillation crystals emit small bursts of visible light when they are struck with γ-rays, and the visible light is converted to electrons by a photocathode of the PMT and the electrical signal is amplified by a dynode string in the PMT.

There are numerous compounds that make suitable scintillation crystals. Bismuth germinate (BGO), barium fluoride (BaFl), gadolinium silicate (GSO), Lutetium orthosilicate (LSO), and Lutetium Yttrium orthosilicate (LYSO) are examples of compounds that form scintillation crystals. In the preferred embodiment, the scintillation crystals include lutetium, so both LSO and LYSO are suitable, as well as other crystal variants containing lutetium.

The subject is injected with a radiopharmaceutical, which for a PET scanner undergoes an annihilation event that emits two 511 eV γ-rays that propagate in opposite directions. That is, the two γ-rays travel in opposite directions along a common ray. In a SPECT scanner, the radiopharmaceutical includes a radioisotope which decays and emits γ-rays of characteristic energy(s).

When the annihilation events occur within the bore 14 of the scanner, is detected as a valid annihilation event if both γ-rays strike detectors substantially simultaneously. In order to validate the event, an event validation processor 20 detects the times that the γ-rays are detected. The γ-rays are subjected to a number of event validation processes that discern valid annihilation events from false ones. For instance, if a second γ-ray is not received in close enough temporal proximity to the first, the first γ-ray is discarded as unpaired. In addition to coincidence detection, the event validation processor 20 can also perform other validation processes, such as energy threshold, and windowing filters, as well as other validation processes known in the art.

Event validation is particularly useful when utilizing detector crystals that contain lutetium in them, such as LSO and LYSO. The lutetium that is used in scintillation crystals for PET imaging naturally includes amounts of a radioactive isotope of lutetium ($Lu^{176}$). This particular isotope of lutetium releases a β particle and three γ-rays when it decays, at 88, 202, and 307 keV. Without event validation procedures, these γ-rays could be mistaken for the γ-rays originating from the subject.

This extra source of radioactivity has been a problem for radiologists since the advent of LSO. It has been the subject of many patent applications attempting to compensate for the extra radioactive source. While the present application still must compensate for the $Lu^{176}$ isotope during the imaging process, it suggests harnessing the extra radioactivity and directing it to beneficial purposes between diagnostic scans.

Figure 2:
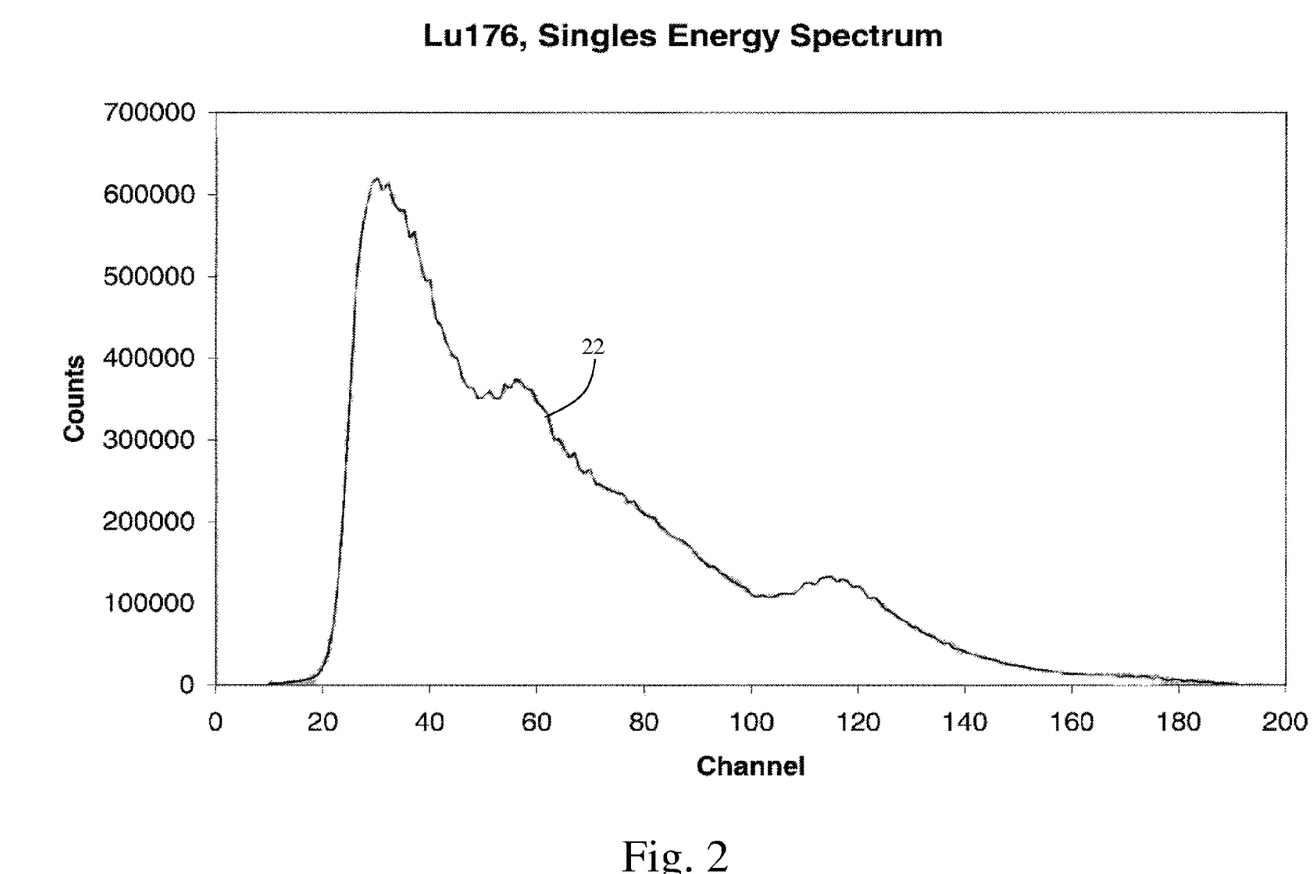
FIG. 2 is an exemplary singles energy spectrum.
Figure 3:
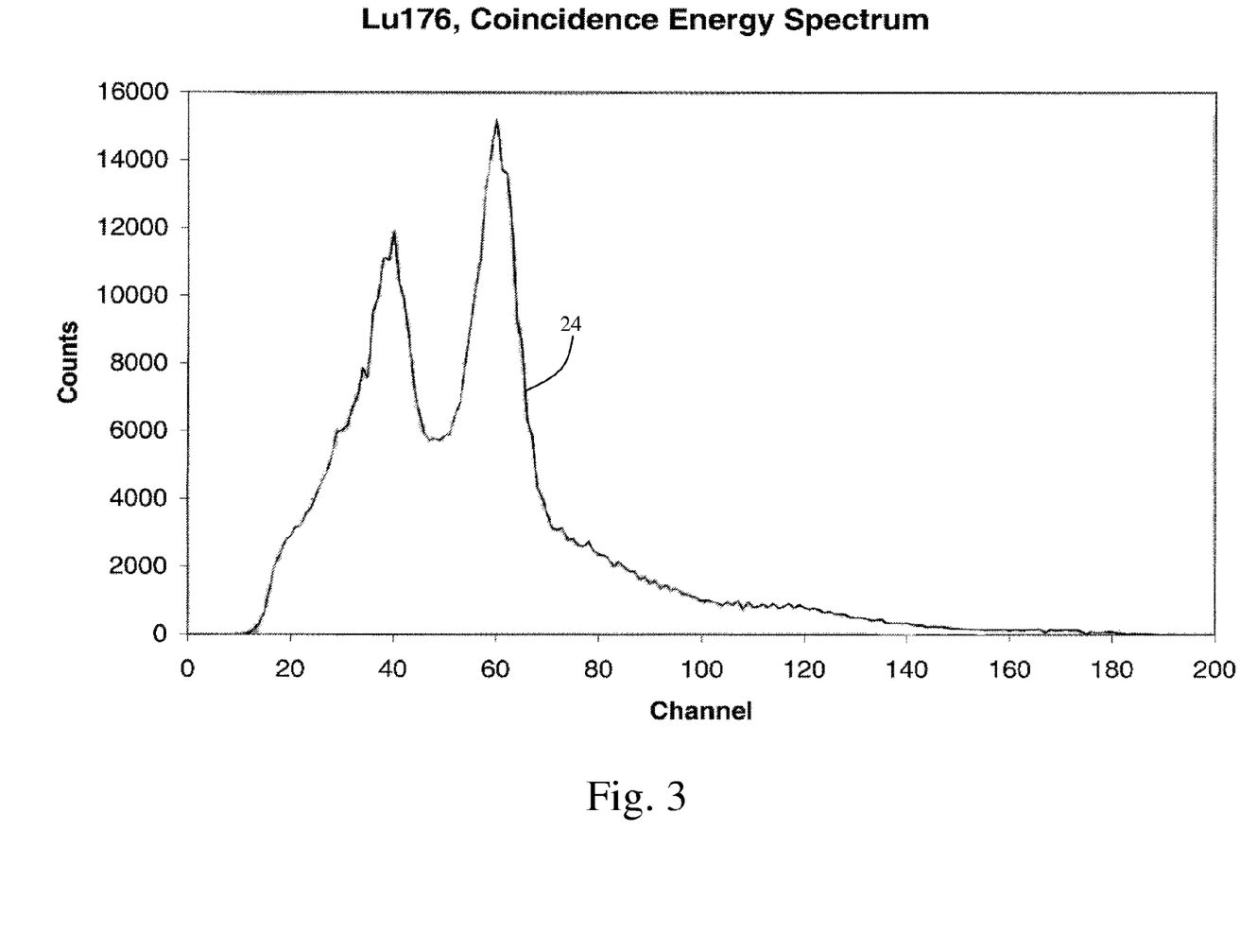
FIG. 3 is an exemplary coincidence energy spectrum.

Coarser calibrations can be performed using the 202 keV peak that appears in a singles energy spectrum 22 in a singles mode, as shown in FIG. 2. Finer calibrations can be performed with a combined energy spectrum 24 that includes the 202 keV peak and a 307 keV peak, as shown in FIG. 3. The light from any given scintillation is typically viewed by a plurality of PMTs. Based on the position of the viewing PMTs and the relative amplitude of the signal from each viewing PMT, a scintillator locator 26 using Anger logic determines the location of each scintillation, i.e. each received γ-ray. Each photomultiplier tube is operated with a gain determined during calibration. Typical gains vary over a range of about 8:1. The gain at which each tube is biased to operate is retrieved from a gain look-up-table (LUT) 28.

To accommodate scintillator light output variation, an amplitude adjustment circuit or processor 30 adjusts the amplitude of each output signal. A preliminary scintillation position is determined to identify the scintillation crystal which received the γ-ray and emits the light scintillation. LSO and LYSO scintillators are commonly an array of individual crystals, e.g., a few centimeters square and each can and typically does produce different levels of light from a given energy radiation event. The amplitude adjustment processor 30 scales the outputs of each PMT that views a given event with a scaling factor for the detecting scintillator from the amplitude correction LUT 32.

A reconstruction processor 34 reconstructs the rays from the accurately located valid events into an image representation of the subject. In PET imaging, the coincidentally detected γ-rays define rays which are reconstructed using known algorithms. In SPECT imaging, a collimator defines a ray corresponding to each scintillation. The reconstruction processor 34 reconstructs the rays into the image using known algorithms. A display monitor 36 displays the reconstructed portions of the subject's anatomy.

Figure 4:
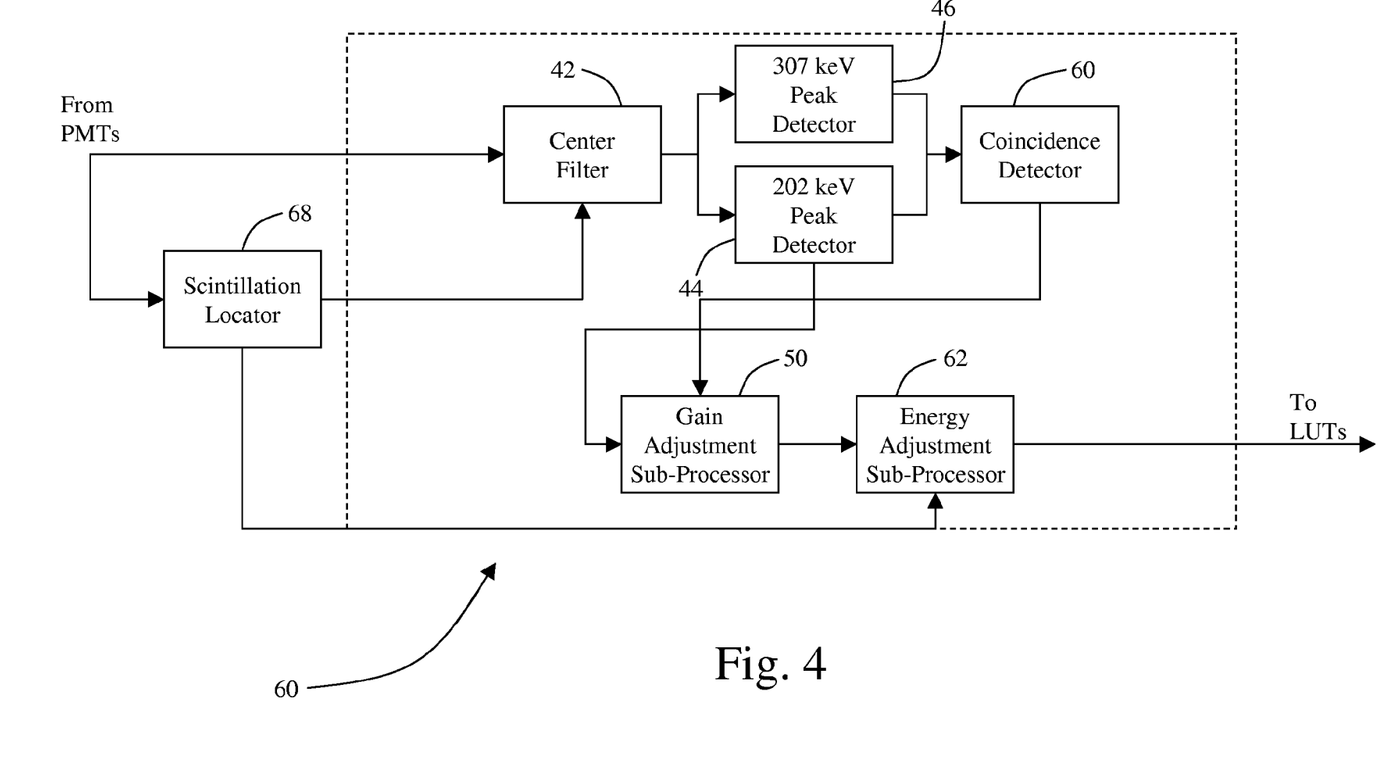
FIG. 4 is a more detailed illustration of a self-calibration processor, in accordance with the present application.
Figure 5:
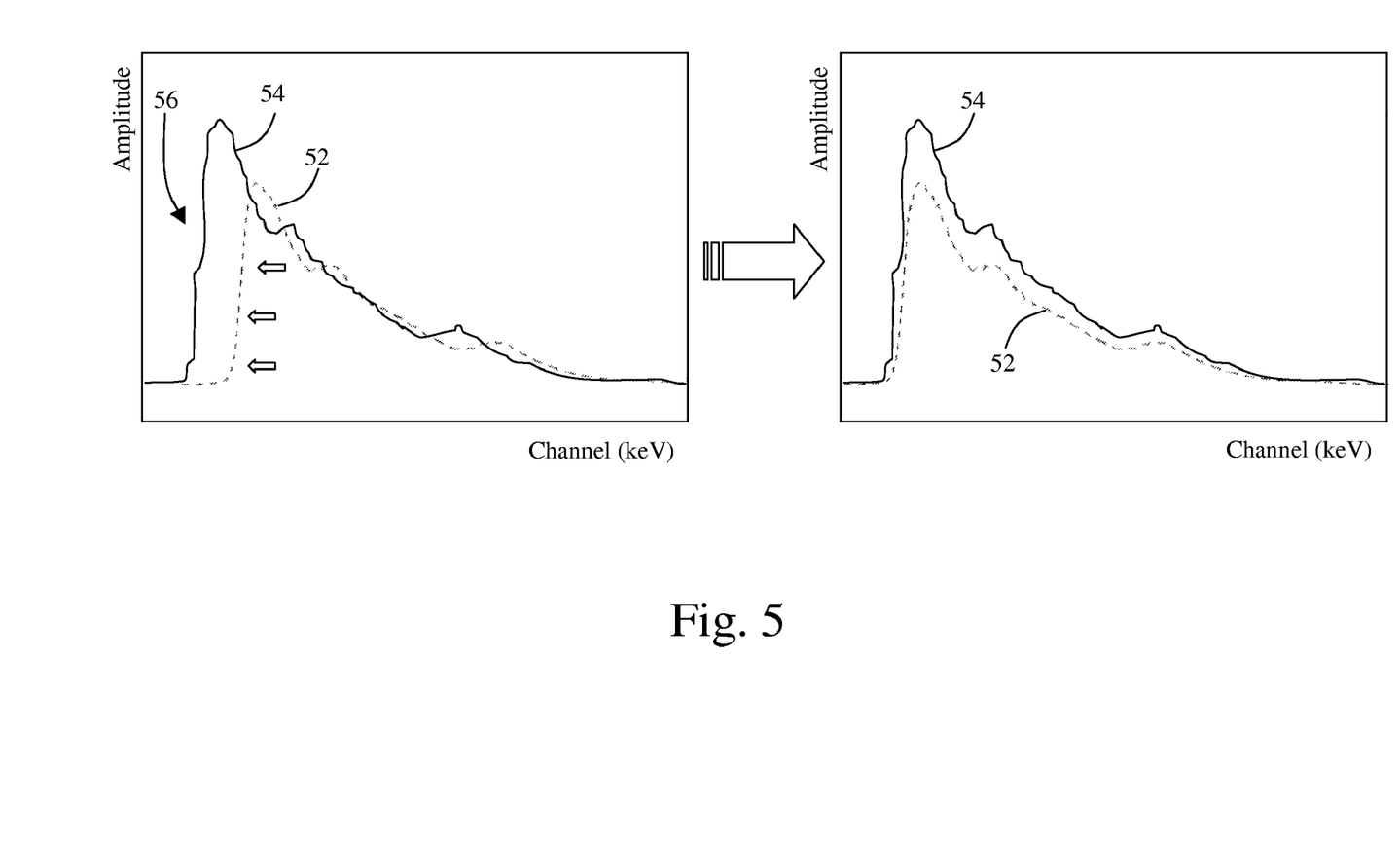
FIG. 5 shows a gain adjustment to a typical singles energy spectrum generated by a PET device.
Figure 6:
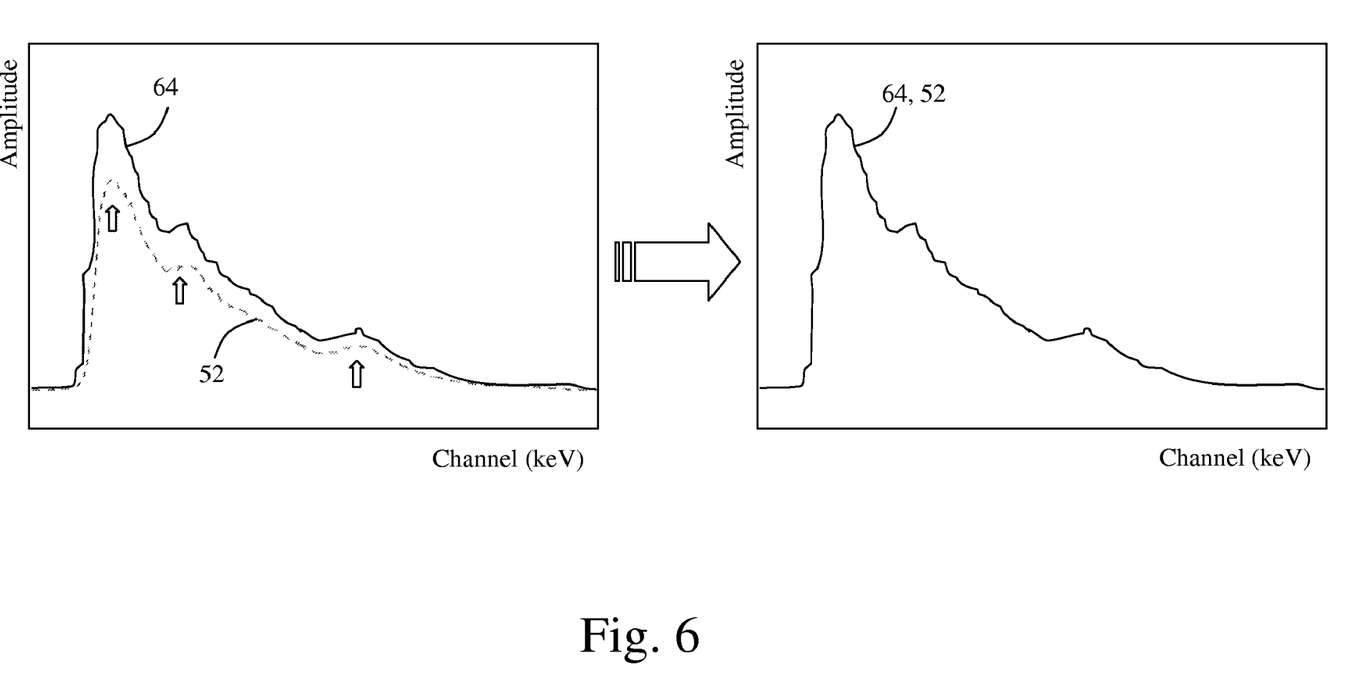
FIG. 6 shows an amplitude adjustment to a typical singles energy spectrum generated by a PET device.

Again, $Lu^{176}$ emits three γ-rays upon its decay, 88 keV, 202 keV, and 307 keV. A self-calibration processor 40 uses this background radiation from radioactive lutetium to calibrate the system 10 when it is not scanning patients. When the system is not scanning a patient, it enters a self-calibration mode that activates the self-calibration processor. With reference to FIGS. 4, 5, and 6, the natural radiation, particularly the 202 keV and the 307 keV γ-rays, escape the scintillator crystal and strike another scintillator causing a scintillation. A center filtering circuit or processor 42 discards any signals that did not originate from substantially centrally under a photomultiplier tube using Anger logic. A 202 keV peak detector 44 and a 307 keV peak detector 46 detect events from γ-rays of corresponding energy from $Lu^{176}$. The 88 keV peak tends not to be as useful because it rarely escapes the crystal in which it was emitted, and windowing thresholds are often higher to distinguish ambient and scattered radiation, etc.

In a first, singles mode embodiment, a gain adjustment sub-processor 50 compares a peak of a received signal, 52 in FIG. 5, to an ideal 202 keV peak 54 and adjusts the gain setting in the gain LUT 26 for the PMT that detected the scintillation accordingly. In the preferred embodiment, with reference to FIG. 5, the gain adjustment sub-processor looks for a characteristic leading edge 56 of the energy pulse. In one embodiment, the leading edge 56 is found by plotting a linear fit to the detected response. Additionally, other polynomials can be used to determine the leading edge 56, along with functions that are tailored to a typical 202 keV response. Regardless of its amplitude or position, the leading edge should be the same for all detected 202 keV γ-rays. That is, even though the amplitude and the energy response of the system PMTs may drift, the tube gain is adjusted such that the 202 keV peak is in the proper channel.

Once the 202 keV, and optionally for a second embodiment, a like 307 keV peak PMT gain calibration procedure is completed, a coincidence mode calibration is optionally performed. Specifically, a coincidence detector 60 detects whether a 202 keV γ-ray is close enough temporally to a 307 keV γ-ray to have been generated in the same $Lu^{176}$ decay event. In the coincidence mode, the coincidence detector 60 detects when a 202 keV γ-ray is detected by one scintillation crystal and a 307 keV γ-ray is detected at a second scintillation crystal near simultaneously. As shown in FIG. 3, the coincidence energy spectrum generates two sharper peaks that are used for finer calibrations of two PMTs simultaneously. That is, the gain for each detecting PMT is adjusted to align the 307 keV precisely with the ideal 307 keV peak, i.e., in the 307 keV energy channel. The gain of the tube receiving the coincident 202 keV event can be adjusted analogously. Because the energy correction is linear, the gain corrections performed by the self-calibration processor 40 accurately translate to the 511 keV peaks used for PET imaging.

After the gain adjustment is calculated and loaded into the gain LUT 26, an energy adjustment sub-processor 62 compares the amplitude of the output signals, i.e., the light output level of the receiving scintillator, in response to a received γ-ray to a nominal or ideal 202 keV γ-ray response 64 and adjusts the scaling factor in the amplitude adjustment look-up table 32 accordingly. Light output from scintillator to scintillator is not consistent, so the sum of the amplitudes of the output signals generated by the viewing PMTs will vary. A scintillator locator 68 uses Anger logic to determine the scintillator which generates each detected event. The energy adjustment sub-processor 62 adjusts the scaling factors for the scintillator that detected the event in the look-up table 32 such that the amplitude of the sum of the output signals are scaled to the nominal response curve 64.

Figure 7:
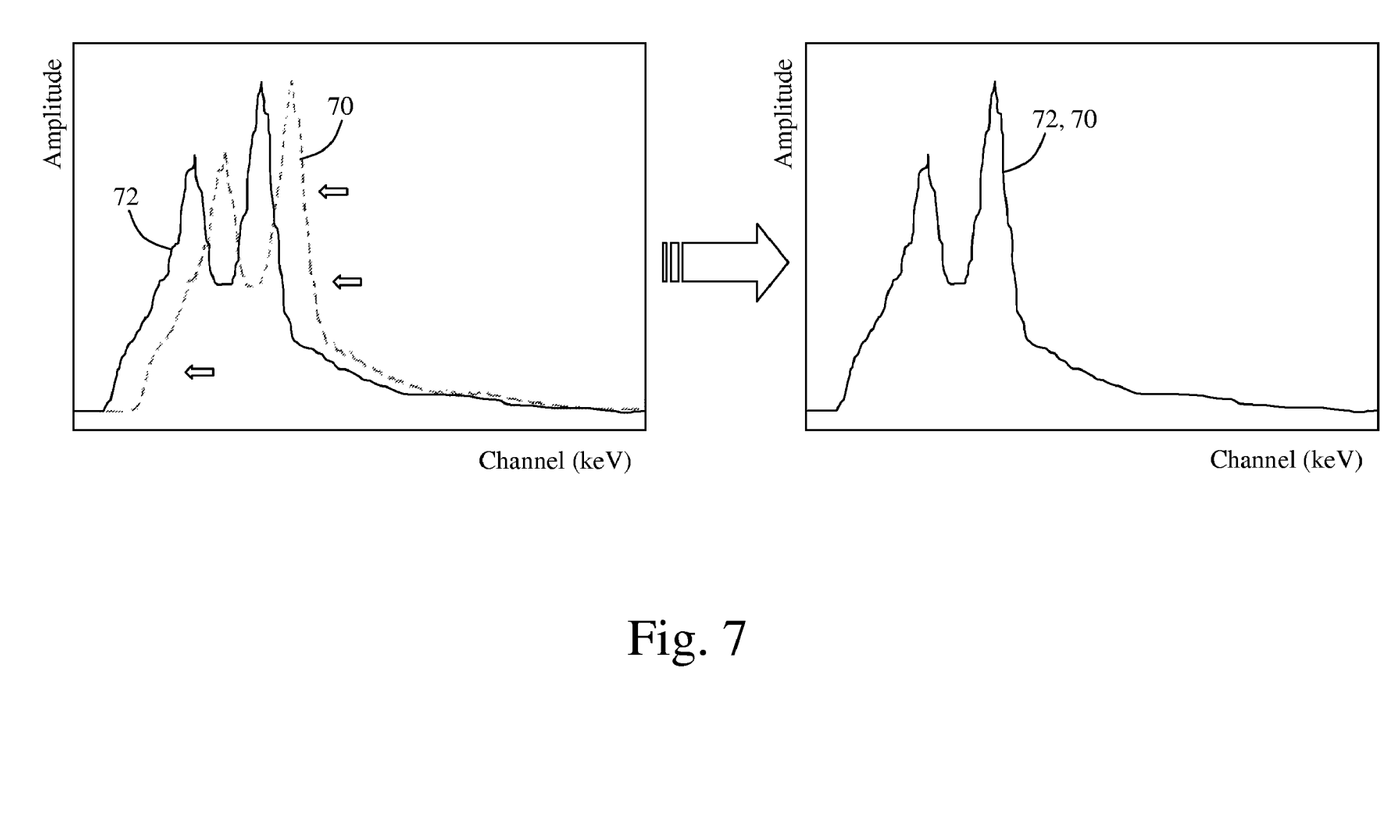
FIG. 7 shows a gain adjustment to a typical coincidence energy spectrum generated by a PET device.

Similarly, with reference to FIG. 7, the calibration described above can be done in coincidence mode. That is, an actual coincidence response 70 is compared against and aligned with a coincidence nominal response 72.

While in the self-calibration mode, the energies detected should only be one of 202 keV and 307 keV, so the filter 42 removes other signals. The PMT gain adjustment is preferably carried out with scintillators that occur substantially directly under a single PMT. This maximizes the amplitude of the output signal from the PMT and facilitates the gain adjustment to this end, the filtering circuit 42 discards events that the scintillator locator 68 determines are not substantially centered under a single PMT.

$Lutetium^{176}$ has a half-life of $3 \times 10^{10}$ years so there is no need to replenish it over the life of the scanner. Other scintillators which naturally contain radioactive elements or which are doped to contain them are also contemplated.

The invention has been described with reference to the preferred embodiments. Modifications and alterations will occur to others upon a reading and understanding of the preceding detailed description. It is intended that the invention be construed as including all such modifications and alterations insofar as they come within the scope of the appended claims or the equivalents thereof.

The invention claimed is:

1. A diagnostic imaging apparatus comprising:
   an array of scintillating elements, each scintillating element emitting light scintillations in response to incident radiation, the scintillating elements exhibiting inherent radioactivity by emitting radiation of at least one characteristic energy;
   an array of photomultiplier tubes in optical communication with the array of scintillating elements, the photomultiplier tubes each generating a response to the light scintillations emitted from the scintillating elements in response to the radiation of the characteristic energy which photomultiplier tube response varies with time and among the photomultiplier tubes
   a gain memory that contains gain settings for each photomultiplier;
   a photomultiplier tube self-calibration processor that recalibrates gain settings for each of the photomultiplier tubes using the inherent radioactivity of the at least one scintillating element, the self-calibration processor determining a characteristic peak in the response detected by one of the photomultiplier tubes in a singles mode, and linearly adjusting the gain setting for the corresponding photomultiplier tube to correct positioning of the characteristic peak in the response signal, the self-calibration processor including a center filter that limits the detected scintillations to scintillations under a center of each photomultiplier tube.

2. The diagnostic imaging apparatus as set forth in claim 1, wherein the self-calibration processor processes at least two characteristic peaks from the response in a coincidence mode and adjusts a gain of a detecting photomultiplier tube accordingly.

3. The diagnostic imaging apparatus as set forth in claim 1, wherein a scintillation light output varies among the scintillators, and further including:
   an amplitude correction memory that contains an amplitude scaling factor for each of the plurality of scintillation elements;
   the self-calibration processor being programmed to:
   identify which of the scintillation elements emitted each light scintillation in response to the incident radiation of the characteristic energy,
   compare an amplitude generated by photomultiplier tube in response to the incident radiation of the characteristic energy to a preselected amplitude level, and
   adjust the scaling factor for the scintillation element which emits the detected light scintillation in response to radiation of the characteristic energy in accordance with the comparing of the generated photomultiplier tube response amplitude with the preselected amplitude level.

4. A diagnostic imaging apparatus comprising:
   an array of scintillating elements that generates scintillation light in response to incident radiation, the scintillating elements exhibiting inherent radioactivity of at least one characteristic energy, a scintillation light output in response to radiation of the at least one characteristic energy varying among the scintillations;
   an amplitude correction memory that contains an amplitude scaling factor for each of a plurality of scintillators;
   an array of photomultiplier tubes in optical communication with the array of scintillating elements, a again of each of the photomultiplier tubes varying over time, the photomultiplier tubes each generating a response to the scintillation light from the scintillating elements, the response to the scintillation light varying with a one of the scintillation elements that generated the light response and a gain of each photomultiplier tube;
   a gain memory that contains gain settings for each photomultiplier;
   a photomultiplier tube self-calibration processor that recalibrates the response of the photomultiplier tubes using the inherent radioactivity of the at least one scintillating element, the self calibration processor being programmed to:
   determine a response peak from the output of a photomultiplier tube in response to a scintillation;

adjust the gain setting in the gain memory for the responding photomultiplier tube which shifts the response peak into alignment with a corresponding peak of a preselected characteristic curve;

determine which of the scintillators generated the scintillation; and, adjust the scaling factor for the generating scintillator to bring an amplitude of the response peak into amplitude correspondence with the corresponding peak of the preselected characteristic curve.

5. The diagnostic imaging apparatus as set forth in claim 4, wherein the at least one scintillating element contains lutetium.

6. The diagnostic imaging apparatus as set forth in claim 5, wherein the inherent radioactivity is resultant from naturally occurring amounts of lutetium 176.

7. The apparatus as set forth in claim 4 wherein the self-calibration processor is further programmed to:

calibrate the response of the photomultiplier tubes during down-time between diagnostic imaging.

8. A method of calibrating a positron emission tomographic (PET) diagnostic imaging scanner comprising:

generating background radiation with an array of scintillating elements that exhibit inherent radioactivity of at least first and second characteristic energies from each decay event;

generating first characteristic energy photonic emissions with the scintillating elements in response to the background radiation of the first characteristic energy emitted by the scintillating elements;

generating second characteristic energy photonic emissions with the scintillation elements in response to background radiation of the second characteristic energy emitted by the scintillating elements;

generating responses to coincident first and second characteris energy photonic emissions with one of the photomultiplier tubes to be calibrated; and calibrating the photomultiplier tubes using the response to the inherent background radiation of the scintillating elements, the calibrating including:

detecting first and second radiation events from a common decay event, determining a characteristic edge of the response of the one photomultiplier tube to the first characteristic energy photonic emission of the common decay event by plotting a fit to a leading edge of a first energy spectrum, determining a characteristic edge of the response of the one photomultiplier tube to the second characteristic energy photonic emission of the common decay event by plotting a fit to a leading edge of a second energy spectrum, determining a first gain correction for the one photomultiplier tube which shifts the response to the first characteristic energy into coincidence with a corresponding characteristic edge of a first energy spectrum, determining a second gain correction for the one photomultiplier tube which shifts the response to the second characteristic energy into coincidence with a corresponding characteristic edge of a second energy spectrum, linearly extrapolating the first and second gain corrections to a 511 keV gain correction, and adjusting a gain of the one of the photomultiplier tubes in accordance with the 511 keV gain correction.

9. The method as set forth in claim 8, wherein scintillating elements the at least array of scintillating elements which have differing light output characteristics, the calibrating step further including:

determining which scintillator of the array generates each photonic emission;

determining an amplitude of the characteristic energy peak in the detecting photomultiplier tube responses;

adjusting an output scaling factor for the generating scintillating which scales the determined amplitude to a preselected amplitude.

10. The method as set forth in claim 9, further including:

storing gain settings for each photomultiplier tube in a gain memory;

storing scaling factors for each scintillation element in an amplitude correction memory; and updating at least one of the gain memory and the amplitude correction memory in the calibrating step.

11. The method as set forth in claim 8, wherein the scintillating elements includes lutetium 176.

12. The method as set forth in claim 8, wherein the step of calibrating occurs during down-time between diagnostic imaging.

13. An apparatus which performs the method of claim 8.

14. The method as set forth in claim 8, wherein the calibrating further includes:

filtering responses of the photomultiplier tubes to limit the responses to responses to photonic emissions from scintillator elements under a center of the one photomultiplier tube.

15. A diagnostic imaging apparatus comprising:

at least one detector assembly including an array of scintillators and an array of photodetectors, the scintillators including a radioactive element which emits radiation with at least one characteristic energy peak, the scintillators exhibiting varying amounts of light output from the radioactivity of the characteristic energy peak;

an amplitude calibration memory which stores scaling factors corresponding to each scintillator for scaling photodetector outputs;

a self calibration processor which receives the photodetector outputs responsive to the radioactive element emitted radiation and adjusts the scaling factors to bring characteristic peak amplitudes of the photodetector outputs to a common amplitude.

16. The diagnostic imaging apparatus as set forth in claim 15, further including:

a gain calibration memory which stores gain settings for each of the photodetectors;

the self calibration circuit further adjusts the gain settings to bring an output peak of each photodetector from responses to radiation of the characteristic energy into alignment with a corresponding characteristic energy peak of a preselected characteristic energy curve.

17. The diagnostic imaging apparatus as set forth in claim 15, wherein each photodetector detects light from a plurality of scintillators of the array, an amplitude of the photodetector output varying with the light output of each scintillator of the array.

18. A diagnostic imaging apparatus comprising:

at least one detector assembly including an array of scintillating elements optically coupled to an array of photodetectors whose response characteristics drift over time, the scintillating element including radioactive elements produce decay events at least at first and second characteristic energies;

a self calibration processor which receives the photodetector outputs responsive to first and second characteristic energy photonic events produced by the decay events and calibrates the photodetectors during down time of the imaging apparatus between imaging sessions which radiation of a third characteristic energy, the calibration processor being programmed to:
  detecting first and second radiation events from a common decay event,
  determining a characteristic edge of the response of the one photomultiplier tube to the first characteristic energy photonic emission of the common decay event by plotting a fit to a leading edge of a first energy spectrum,
  determining a characteristic edge of the response of the one photomultiplier tube to the second characteristic energy photonic emission of the common decay event by plotting a fit to a leading edge of a second energy spectrum,
  determining a first gain correction for the one photomultiplier tube which shifts the response to the first characteristic energy into coincidence with a corresponding characteristic edge of a first energy spectrum,
  determining a second gain correction for the one photomultiplier tube which shifts the response to the second characteristic energy into coincidence with a corresponding characteristic edge of a second energy spectrum,
  linearly extrapolating the first and second gain corrections to a 511 keV gain correction, and
  adjusting the gain of the one of the photomultiplier tubes in accordance with the 511 keV gain correction.

* * * * *